United States Patent [19]

Urawa et al.

[11] Patent Number: 5,665,888
[45] Date of Patent: Sep. 9, 1997

[54] PROTECTED AMINOTHIAZOLYLACETIC ACID DERIVATIVES

[75] Inventors: Yoshio Urawa; Akihiko Shimotani; Takeo Kanai, all of Ibaraki Prefecture; Masahiko Tsujii, Chiba Prefecture, all of Japan

[73] Assignee: Eisai Chemical Co., Ltd., Ibaraki Prefecture, Japan

[21] Appl. No.: 412,190

[22] Filed: Mar. 28, 1995

[30] Foreign Application Priority Data

Mar. 30, 1994 [JP] Japan ................. 6-082619
Jun. 22, 1994 [JP] Japan ................. 6-139918
Nov. 17, 1994 [JP] Japan ................. 6-283543

[51] Int. Cl.$^6$ ............................................. C07D 277/42
[52] U.S. Cl. ........................................................ 548/194
[58] Field of Search ............................................ 548/194

[56] References Cited

U.S. PATENT DOCUMENTS 4,713,461 12/1987 Onove ........................... 548/194

*Primary Examiner*—Robert Gerstl
*Attorney, Agent, or Firm*—Wenderoth, Lind & Ponack

[57] ABSTRACT

Described is a protected aminothiazolylacetic acid derivative represented by the following formula (I):

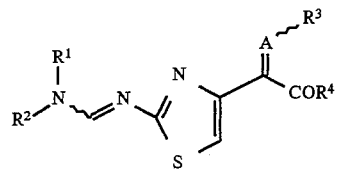

wherein A represents a nitrogen atom or a methine group, $R^1$ and $R^2$ may be the same or different and individually represent a hydrogen atom, a lower alkyl group or a substituted or unsubstituted aryl group, $R^3$ represents a lower alkoxy group, a halogenated lower alkoxy group, a triphenylmethoxy group, a lower alkyl group or an acyloxy group, and $R^4$ represents a halogen atom, a hydroxy group, a lower alkoxy group or a substituted or unsubstituted amino group; and salts thereof; as well as processes for the preparation thereof. The protected aminothaizolylacetic acid derivative according to the present invention is an useful intermediate for introducing a 2-(2-aminothiazol-4-yl)-2-alkoxyiminoacetyl group or a 2-(2-aminotiazol-4-yl)-2-alkenoyl group into a cephem skeleton.

1 Claim, No Drawings

PROTECTED AMINOTHIAZOLYLACETIC ACID DERIVATIVES

BACKGROUND OF THE INVENTION a) Field of the Invention

The present invention relates to protected aminothiazolyl acetic acid derivatives and salts thereof, which are preparation intermediates useful for introducing a 2-(2-aminothiazol-4-yl)-2-alkoxyiminoacetyl group or a 2-(2-aminothiazol-4-yl)-2-alkenoyl group into a cephem skeleton, and also to a process for the preparation thereof. The above alkoxyiminoacetyl group or alkenoyl group is a moiety common to antibiotics such as Cefmenoxime, Cefpodoxime proxetil, Cefepime, Cefpirome, Cefzopran, Cefclidine, DQ-2556 (CAS Registry No.102253-70-3), FK-037 (CAS Registry No. 122841-12-7), E1077 (CAS Registry No.11685B-25-9), and S-1108 (CAS Registry No.105889-45-0), and the like.

b) Description of the Related Art

Antibiotics such as Cefmenoxime, Cefpodoxime proxetil, Cefepime, Cefpirome, Cefzopran, Cefclidine, DQ-2556, FK-037 and E1077 and the like contain a 2-(2-aminothiazol-4-yl)-2-alkoxyiminoacetyl group or a 2-(2-aminothiazol-4-yl)-2-alkenoyl group as a common moiety in their molecules. To obtain still higher antibacterial activities, this substituent is essential.

c) Prior Art

Upon introducing a 2-(2-aminothiazol-4-yl)-2-alkoxyiminoacetyl group or a 2-(2-aminothiazol-4-yl)-2-alkenoyl group into the cephem skeleton for the preparation of an acid amide, it has heretofore been the practice to use an active derivative, such as an acid chloride, mixed acid anhydride or active ester and the like of a 2-(2-aminothiazol-4-yl)-2-alkoxyiminoacetic acid or a 2-(2-aminothiazol-4-yl)-2-alkenoic acid, especially a 2-(2-aminothiazol-4-yl)-2-alkoxyiminoacetyl chloride or a 2-(2-aminothiazol-4-yl)-2-alkenoic acid chloride. Refer to Japanese Patent Application Laid-oepn Nos.123,189/87, 264,471/88, 264,470/88, 156,982/89, and the like.

A conventional preparation process is shown by the following reaction sheme:

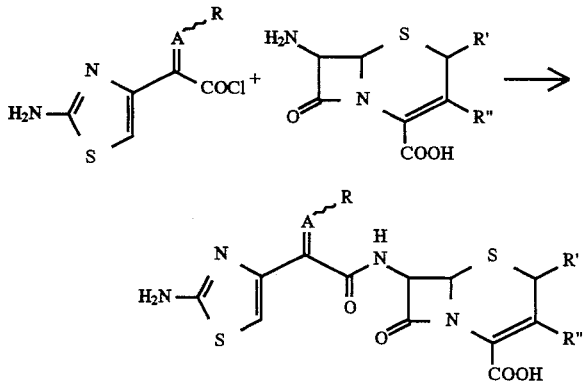

wherein A represents a nitrogen atom or a methine group, R represents a lower alkoxy group, a halogenated lower alkoxy group, a triphenylmethoxy group, a lower alkyl group or an acyloxy group, and R' and R" individually represent a hydrogen atom or a substituent group.

Conventional active derivatives including 2-(2-aminothiazol-4-yl)-2-alkoxyiminoacetyl chloride have nucleophilic reactivity, because the amino group on the thiazole ring is not protected. Therefore, the active derivative is prepared or when the amino group is reacted with the cephem skeleton to form an acid amide, a side reaction takes place on the amino group, resulting in that a high-purity active derivative or acid amide could not be obtained in a good yield. Antibiotics, as pharmaceuticals, are required to have particularly high quality. In many cases, it is therefore necessary to conduct plural purification steps. The use of these active derivatives therefore has not been considered as an industrially suited preparation process.

To control the above-described side reaction on the amino group, it is preferred to protect the amino acid in advance. A number of protecting groups are known for the amino group. No protecting group is however known to have stability in various reactions and readily removable property under mild conditions, as well as economical merits. Upon conducting a target investigation with a view toward inter alia improving the purity of a product, reducing its production cost and improving the process operability, it was found that such conventional amino-protecting groups are improper. In order to achieve the target, there has been desidered the development of a novel protected aminothiazolylacetic acid derivative.

SUMMARY OF THE INVENTION

The inventors have proceeded with extensive research, with a view toward developing a novel protected aminothiazolyl acetic acid derivative which is useful in introducing a 2-(2-aminothiazol-4-yl)-2-alkoxyiminoacetyl group or a 2-(2-aminothiazol-4-yl)-2-alkenoyl group into the cephem skeleton to prepare an acid amide and also permits an improvement in the purity of the product, a reduction in the product cost, an improvement in the process operability and the like. As a result, it has been found that a protected aminothiazolyl acetic acid derivative represented by the below-described formula (I) or a salt thereof can attain the above-described object, leading to the completion of the present invention.

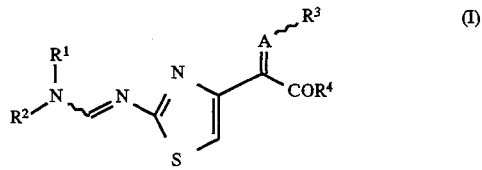

wherein A represents a nitrogen atom or a methine group, $R^1$ and $R^2$ may be the same or different and individually represent a hydrogen atom, a lower alkyl group or a substituted or unsubstituted aryl group, $R^3$ represents a lower alkoxy group, a halogenated lower alkoxy group, a triphenylmethoxy group, a lower alkyl group or an acyloxy group, and $R^4$ represents a halogen atom, a hydroxyl group, a lower alkoxy group or a substituted or unsubstituted amino group.

The present invention therefore provides a novel protected aminothiazolylacetic acid derivative (I) or a salt thereof which is useful for introducing a 2-(2-aminothiazol-4-yl)-2-alkoxyiminoacetyl group or a 2-(2-aminothiazol-4-yl)-2-alkenoyl group which is a moiety common to antibiotics such as Cefmenoxime, Cefpodoxime proxetil, Cefepime, Cefpirome, Cefzopran, Cefclidine, DQ-2556, FK-037 and E1077, and the like and also a process for the preparation thereof.

The present invention provides the following two processes for the preparation of the protected aminothiazolylacetic acid (I) or the salt thereof:

(1) One process of route comprises reacting an aminothiazolylacetic acid derivative (II) represented by the following formula (II):

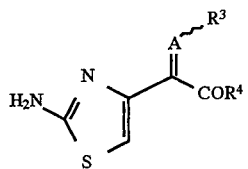

wherein A, $R^3$ and $R^4$ have the same meanings as defined above, or a salt thereof with a (halogenated methylene)-dialkylammonium halide represented by the following formula (III):

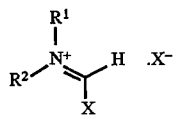

wherein $R^1$ and $R^2$ have the same meanings as defined above and X represents a halogen atom.

(2) The other process of route comprises effecting a reaction of an aminothiazolylacetic acid derivative (II) in a liquid mixture of a formamide derivative represented by the following formula (IV):

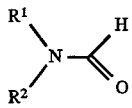

wherein $R^1$ and $R^2$ have the same meanings as defined above, and a chlorinating agent selected from phosphorus oxychloride, phosgene, diphosgene, triphosgene or oxalyl chloride.

The novel protected thiazolylacetic acid derivative (I) or the salt thereof according to the present invention has made it possible to meet the requirements and desires described above.

DETAILED DESCRIPTION OF THE INVENTION AND PREFERRED EMBODIMENTS

The protected aminothiazolylacetic acid derivative according to the present invention is represented by the following formula (I):

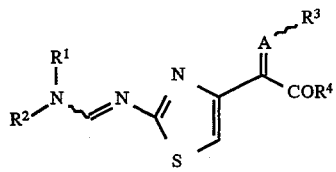

wherein A represents a nitrogen atom or a methine group, $R^1$ and $R^2$ may be the same or different and individually represent a hydrogen atom, a lower alkyl group or a substituted or unsubstituted aryl group, $R^3$ represents a lower alkoxy group, a halogenated lower alkoxy group, a triphenylmethoxy group, a lower alkyl group or an acyloxy group, and $R^4$ represents a halogen atom, a hydroxy group, a lower alkoxy group or a substituted or unsubstituted amino group.

In the above formula (I), the "methine group" in the definition for A means a group represented by the formula =CH—. The "lower alkyl group" in the definitions for $R^1$, $R^2$, $R^3$ and $R^4$ may more specifically mean an alkyl group having 1–6 carbon atoms, for example, a methyl, ethyl, n-propyl, i-propyl, n-butyl, i-butyl, t-butyl, pentyl or hexyl group and the like. In the definition for $R^3$, the "lower alkoxy group" may more specifically mean a group formed of the above-described lower alkyl group and an oxygen atom bonded therewith, such as a methoxy, ethoxy, propoxy, butoxy, pentyloxy or hexyloxy group, and the like. The "triphenylmethoxy group" means the group represented by the formula [—OC($C_6H_5$)$_3$], and the "acyloxy group" may more specifically mean a group derived from a linear or branched fatty acid having 1–6 carbon atoms, for example, a formyloxy, acetoxy, propionyloxy, butyryloxy, valeryloxy or hexanoyloxy group and the like. The "halogen atom" in the definition for $R^4$ may mean a chlorine, bromine, iodine or fluorine atom. The "halogenated lower alkoxy group" in the definition for $R^3$, means the above-described lower alkoxy group with some or all of its hydrogen atoms having been substituted by halogen atom(s), such as a chloromethoxy, bromomethoxy, fluoromethoxy, difluoromethoxy, trifluoromethoxy, fluoroethoxy or fluoropropoxy group and the like. The "substituted or unsubstituted amino group" in the definition for $R^4$, means, for example, an amino, methylamino, dimethylamino, ethylamino, diethylamino, propylethylamino, pyrrolidyl, piperidyl, anilino (—NH—$C_6H_5$), methylanilino (—NCH$_3$—$C_6H_5$), benzylamino (—NH—CH$_2C_6H_5$) or phenethylamino [—NH—CH$_2$CH$_2C_6H_5$ or —NH—CH(CH$_3$)$C_6H_5$] group and the like. Among these, more preferred are a methyl or ethyl group for $R^1$ and $R^2$, a methoxy, fluoromethoxy or trifluoromethoxy group for $R^3$ when A is a nitrogen atom; or an ethyl group for $R^3$ when A is a methine group; and a hydroxy group or a chlorine or bromine atom for $R^4$.

The protected aminothiazolylacetic acid derivative (I) includes, as shown below, a Syn-isomer (Z-isomer) and an Anti-isomer (E-isomer) as geometric isomers with respect to an imino or methylidene group represented by =A–$R^3$ in the formula (I). No particular limitation is however imposed on the isomerism in the present invention, so that the protected aminothiazolylacetic acid derivative (I) can be one of these geometric isomers.

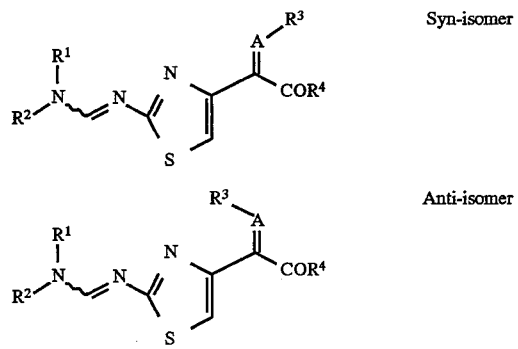

wherein A, $R^1$, $R^2$, $R^3$ and $R^4$ have the same meanings as defined above.

Further, the protected aminothiazolylacetic acid derivative (I) also includes, as shown below, a Syn-isomer (Z-isomer) and an Anti-isomer (E-isomer) as geometric isomers with respect to an aminomethylidenamino group represented by $R^1R^2$N–CH=N— in the formula (I). No particular limitation is however imposed on the isomerism in the present invention, so that the protected aminothiazolylacetic acid derivative (I) can be one of these geometric isomers.

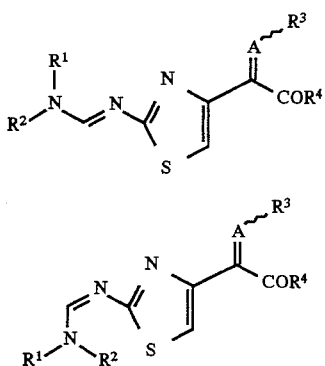

Syn-isomer

Anti-isomer wherein A, $R^1$, $R^2$, $R^3$ and $R^4$ have the same meanings as defined above.

In the protected aminothiazolylacetic acid derivative (I) according to the present invention, the respective compounds have four geometric isomers depending upon the configuration of the imino group, methylidene group or aminomethylidenamino group. Needless to say, these isomers are all included in the present invention.

No particular limitation is imposed on the salt of the protected aminothiazolylacetic acid derivative (I), insofar as it can be formed in a manner known per se in the art. Practical examples include addition salts such as the hydrochloride, hydrobromide and hydroiodide and the like.

The following compounds can be mentioned as more specific examples of the protected amiothiazolylacetic acid derivative (I), although the protected aminothiazolylacetic acid derivative (I) in the present invention is not limited thereto.

(1) 2-(2-Dimethylaminomethylidenaminothiazol-4-yl)-2-methoxyiminoacetyl chloride;
(2) 2-(2-Dimethylaminomethylidenaminothiazol-4-yl)-2-methoxyiminoacetyl bromide;
(3) 2-(2-Dimethylaminomethylidenaminothiazol-4-yl)-2-methoxyiminoacetyl iodide;
(4) 2-(2-Diethylaminomethylidenaminothiazol-4-yl)-2-methoxyiminoacetyl chloride;
(5) 2-(2-Dimethylaminomethylidenaminothiazol-4-yl)-2-trifluoromethoxyiminoacetyl chloride;
(6) 2-(2-Dimethylaminomethylidenaminothiazol-4-yl)-2-methoxyiminoacetic acid;
(7) 2-(2-Dimethylaminomethylidenaminothiazol-4-yl)-2-trifluoromethoxyiminoacetic acid;
(8) Methyl 2-(2-dimethylaminomethylidenaminothiazol-4-yl)-2-methoxyiminoacetate;
(9) Butyl 2-(2-dimethylaminomethylidenaminothiazol-4-yl)-2-methoxyiminoacetate;
(10) 2-(2-Dimethylaminomethylidenaminothiazol-4-yl)-2-methoxyiminoacetamide;
(11) N-Phenethyl-2-(2-dimethylaminomethylidenaminothiazol-4-yl)-2-methoxyiminoacetamide;
(12) 2-[2-(N-Methyl-N-phenyl)aminomethylidenaminothiazol-4-yl]-2-methoxyiminoacetic acid;
(13) 2-[2-(N-Methyl-N-phenyl)aminomethylidenaminothiazol-4-yl]-2-methoxyiminoacetyl chloride;
(14) Ethyl 2-[2-(N-methyl-N-phenyl)aminomethylidenaminothiazol-4-yl]-2-methoxyiminoacetate;
(15) 2-[2-(N-Methyl-N-phenyl)aminomethylidenaminothiazol-4-yl]-2-methoxyiminoacetamide;
(16) 2-(2-Dimethylaminomethylidenaminothiazol-4-yl)-2-pentenoic acid;
(17) 2-(2-Dimethylaminomethylidenaminothiazol-4-yl)-2-pentenoyl chloride;
(18) Ethyl 2-(2-dimethylaminomethylidenaminothiazol-4-yl)-2-pentenoate;
(19) 2-(2-Dimethylaminomethylidenaminothiazol-4-yl)-2-pentenoamide;
(20) 2-[2-(N-Methyl-N-phenyl)aminomethylidenaminothiazol-4-yl]-2-pentenoic acid;
(21) 2-[2-(N-Methyl-N-phenyl)aminomethylidenaminothiazol-4-yl]-2-pentenoyl chloride;
(22) Ethyl 2-[2-(N-methyl-N-phenyl)aminomethylidenaminothiazol-4-yl]-2-pentenoate; and
(23) 2-[2-(N-Methyl-N-phenyl)aminomethylidenaminothiazol-4-yl]-2-pentenoamide.

An amiothiazolylacetic acid derivative (II) to be used in the present invention can be represented by the following formula (II):

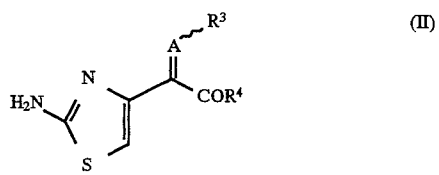

wherein A, $R^3$ and $R^4$ have the same meanings as defined above. Specific examples of the aminothiazolylacetic acid derivative (II) include the following compounds, although the aminothiazolylacetic acid derivative (II) in the present invention is not limited thereto.

(1) 2-(2-Aminothiazol-4-yl)-2-methoxyiminoacetic acid;
(2) 2-(2-Aminothiazol-4-yl)-2-trifluoromethoxyiminoacetic acid;
(3) 2-(2-Aminothiazol-4-yl)-2-methoxyiminoacetyl chloride;
(4) 2-(2-Aminothiazol-4-yl)-2-methoxyiminoacetyl bromide;
(5) 2-(2-Aminothiazol-4-yl)-2-methoxyiminoacetyl iodide;
(6) 2-(2-Aminothiazol-4-yl)-2-acethoxyiminoacetyl chloride;
(7) 2-(2-Aminothiazol-4-yl)-2-trifluoromethoxyiminoacetyl chloride;
(8) Methyl 2-(2-aminothiazol-4-yl)-2-methoxyiminoacetate;
(9) Butyl 2-(2-aminothiazol-4-yl)-2-methoxyiminoacetate;
(10) 2-(2-Aminothiazol-4-yl)-2-methoxyiminoacetamide;
(11) N-Phenethyl-2-(2-aminothiazol-4-yl)-2-methoxyiminoacetamide;
(12) 2-(2-Aminothiazol-4-yl)-2-pentenoic acid;
(13) 2-(2-Aminothiazol-4-yl)-2-pentenoyl chloride;
(14) Ethyl 2-(2-aminothiazol-4-yl)-2-pentenoate; and
(15) 2-(2-Aminothiazol-4-yl)-2-pentenoamide.

A (halogenated methylene)-dialkylammonium halide to be used in the present invention can be represented by the following formula (III):

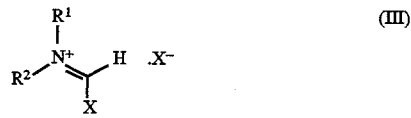

wherein $R^1$ and $R^2$ have the same meanings as defined above and X represents a halogen atom. Specific examples of the (halogenated methylene)-dialkylammonium halide (III) include the following compounds, although the (halogenated methylene)-dialkylammonium halide (III) in the present invention is not limited thereto.

(1) (Chloromethylene)dimethylammonium chloride [popular name: Arnold's reagent];
(2) (Bromomethylene)dimethylammonium bromide;
(3) (Chloromethylene)dimethylammonium chloride;
(4) (Bromomethylene)diethylammonium bromide; and
(5) (Chloromethylene)methylphenylammonium chloride.

These (halogenated methylene)-dialkylammonium halides (III) are available as organic synthesis reagents or industrial raw materials (products of SNPE Inc.), and can also be synthesized by the process disclosed, for example, in "Chemical industry" 16, 664–5, 1974 or "Nucleic Acid Chemistry" vol 2, 989–92 (1978), John Wiley & Sons, Inc., New York, N.Y., U.S.A.

The formamide derivative to be used in the present invention is represented by the following formula (IV):

     (IV)

wherein $R^1$ and $R^2$ have the same meanings as defined above. Specific examples of the formamide derivative (IV) include the following compounds, although the formamide derivative (IV) in the present invention is not limited thereto.
(1) N,N-dimethylformamide;
(2) N,N-diethylformamide;
(3) N-ethyl-N-propylformamide;
(4) N,N-dipropylformamide;
(5) Formamide; and
(6) N-methylformanilide.

The process of the present invention for the preparation of the protected aminothiazolylacetic acid derivative (I) will hereinafter be described in detail. The process can be practiced either in the following two process of routes (1) and (2). In whichever route the process is carried out, the protected aminothiazolylacetic acid derivative (I) can be obtained.

(1) The aminothiazolylacetic acid derivative (II) or a salt thereof is reacted with the (halogenated methylene)-dialkylammonium halide (III).

(2) The aminothiazolylacetic acid derivative (II) or a salt thereof is reacted in a liquid mixture selected from the following combinations:
formamide derivative (IV) and phosphorus oxychloride;
formamide derivative (IV) and phosgene;
formamide derivative (IV) and diphosgene,
formamide derivative (IV) and triphosgene; or
formamide derivative (IV) and oxalyl chloride.

Here, the term "diphosgene" means trichloromethyl chloroformate (CAS Registry No. 503-38-8) represented by the following chemical formula:

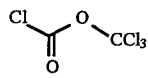

It is available as a regent or an industrial raw material. Further, the term "triphosgene" means ditrichloromethyl carbonate (CAS Registry No. 32315-10-9) represented by the following chemical formula:

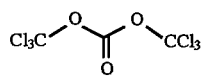

It is available as a reagent or an industrial raw material. Alternatively it can be synthesized according to the process disclosed in "Angew. Chem." 99 (9), 922–3, 1987.

Route (1)

In this route, the process can be practiced generally according to the preparation process of an imine as disclosed in U.S. Pat. No. 4,652,644. In the present invention, it is preferred to dissolve a (halogenated methylene)-dialkylammonium halide (III) in a solvent and subsequent to the addition of an aminothiazolylacetic acid derivative (II) or a salt thereof, followed by stirring the resulting mixture.

Although no particular limitation is imposed on the amount of the (halogenated methylene)-dialkyl-ammonium halide (III) to be used, it is used generally in an amount of 0.9–5.0 equivalents, preferably in an amount of 0.95–3.0 equivalents, more preferably in an amount of 1.0–2.0 equivalents relative to the aminothiazolylacetic acid derivative (III). However, where the aminothiazolylacetic acid derivative (II) is a carboxylic acid ($R^4$=OH), it is used generally in an amount of 1.9–10.0 equivalents, preferably 1.95–6.0 equivalents, more preferably 2.0–2.0 equivalents.

No particular limitation is imposed on the solvent insofar as it is inert to the (halogenated methylene)-dialkylammonium halide (III) or the aminothiazolylacetic acid derivative (II). Specific examples of generally usable solvents include tetrahydrofuran, 1,2-dimethoxyethane, ethyl ether, isopropyl ether, dioxane, dioxolan, methyl acetate, ethyl acetate, propyl acetate, isopropyl acetate, butyl acetate, methyl propionate, ethyl butyrate, pyridine, chloroform, methylene chloride, dichloroethane, trichloroethane and the like. Of these, more preferred are, but are not limited to, tetrahydrofuran, methyl acetate and isopropyl ether. Although no particular limitation is imposed on the amount of the solvent to be used, the solvent is used generally in an amount of 1.0–50 ml, preferably 1.5–0 ml, more preferably 2.0–30 ml per gram of the (halogenated methylene)-dialkylammonium halide (III).

The reaction temperature is not limited either. The reaction can be carried out generally at from −78° C. to the refluxing temperature of the solvent. It is however preferred to conduct the reaction at a temperature of from −40° C. to room temperature, with a low temperature of from −20° to 0° C. being more preferred.

Although the reaction time may vary depending on the amounts of the (halogenated methylene)-dialkyl ammonium halide (III) or the solvent to be used and also on the reaction temperature, the reaction is generally completed within from 10 minutes to 3 hours or so.

Route (2)

In this route, the process can be practiced according to the method generally known as the "Vilsmeyer reaction". In the present invention, however, it is preferred to add dropwise or blow a chlorinating agent selected from phosphorus oxychloride, phosgene, diphosgene, triphosgene and oxazyl chloride into the formamide derivative (IV) under cooling, followed by, still under cooling, condition reacting the resultant liquid mixture with a solution of the aminothiazolylacetic acid derivative (II) or its salt.

Although no particular limitation is imposed on the amount of the formamide derivative (IV) to be employed in the present reaction, the formamide derivative (IV) is generally employed in an amount of 0.9–50 equivalents, preferably 0.95–30 equivalents, more preferably 1.0–20 equivalents relative to the aminothiazolylacetic acid derivative (II). No limitation is imposed on the amount of the chlorinating agent such as phosphorus oxychloride, and the like. The chlorinating agent can however be used generally in an amount of 0.9–50 equivalents, preferably 0.95–3.0 equivalents, more preferably 1.0–2.0 equivalents relative to the aminothiazolylacetic acid derivative (II).

No particular limitation is imposed on the solvent insofar as it is inert to the formamide derivative (IV), the halogenating agent such as phosphorus oxychloride, and the like or the aminothiazolylacetic acid derivative (II). It is also possible to dispense with the other solvent by using the formamide derivative (IV) in an excess amount. When a solvent is used, specific examples of generally usable solvents may include tetrahydrofuran, 1,2-dimethoxyethane, ethyl ether, isopropyl ether, dioxane, dioxolan, chloroform, methylene chloride, dichloroethane, and trichloroethane and the like. Although no particular limitation is imposed on the amount of the solvent, the solvent is employed generally in an amount of 1.0–50 ml preferably 1.5–40 ml, more preferably 2.0–30 ml per gram of the aminothiazolylacetic acid derivative (II).

The reaction temperature is not limited either. The reaction can be carried out generally at −78° C. to the refluxing temperature of the solvent, preferably from −40° C. to room temperature, more preferably from −20° C. to 10° C.

Although the reaction time may vary depending on the amounts of the formamide derivative (IV), the halogenating agent such as phosphorus oxychloride or the solvent to be used and also on the reaction temperature, the reaction is generally completed within from 10 minutes to 6 hours or so.

The protected aminothiazolylacetic acid derivative (I) so obtained can be isolated and purified by a method known per se in the art, for example, by crystallization when it is in the form of an acid halide, or by recrystallization, silica gel column chromatography, HPLC or the like when it is a carboxylic acid, an ester or an acid amide.

Further, deprotection of the dimethylaminomethylidene group as a protecting group to form an amino group can be conducted by hydrolyzing it under acidic or basic conditions.

EXAMPLES

The following examples are given to describe the present invention more practically. Needless to say, the present invention is by no means limited by them.

Example 1

Synthesis of (Z)-2-(2-dimethylaminomethylidenaminothiazol-4-yl)-2-methoxyiminoacetyl chloride.hydrochloride

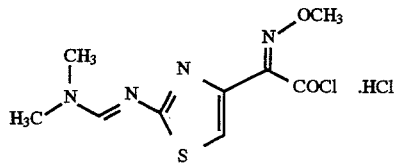

Dimethylaminochloromethyleneammonium chloride (496 mg, 3.87 mmol) was dissolved in 10 ml of tetrahydrofuran, followed by cooling to −10° C. Added to the solution were 870 mg (3.2 mmol) of (Z)-2-(2-aminothiazol-4-yl)-2-methoxyiminoacetyl chloride hydrochloride and the resulting mixture was stirred for 40 minutes. The reaction mixture was concentrated under reduced pressure. Deposited crystals were collected by filtration under a nitrogen gas stream and then dried at room temperature, whereby 497 mg of the title compound were obtained (yield: 47%).
Syn-isomer
$^1$H-NMR (DMSO-$d_6$, 400 MHz); δ (ppm): 8.68(1H,s), 7.56(1H,s), 3.91(3H,s), 3.37(3H,s), 3.30(3H,s).
Elemental analysis:

|   | Calculated | Found |
|---|---|---|
| H | 3.89% | 3.94% |
| C | 34.74% | 34.79% |
| N | 18.00% | 17.71% |

Quantitated amount of chlorine (ion chromatograph):
Calculated: 22.8% Found: 23.1%

Example 2

Synthesis of (Z)-2-(2-dimethylaminomethylidenaminothiazol-4-yl)-2-methoxyiminoacetyl chloride.hydrochloride Dimethylaminochloromethyleneammonium chloride (1.52 g, 12.0 mmol) was dissolved in 7 ml of tetrahydrofuran, followed by cooling to −12° C. Added to the solution were 1.10 g (5.5 mmol) of (Z)-2-(2-aminothiazol-4-yl)-2-methoxyiminoacetic acid and the resulting mixture was stirred for 40 minutes. Isopropyl ether (16 ml) was added to the reaction mixture, followed by stirring for 40 minutes. Deposited crystals were collected under a nitrogen gas stream, collected by filtration and then dried, whereby 1.65 g of the title compound were obtained (yield: 96.9%).

Example 3

Synthesis of (Z)-2-(2-dimethylaminomethylidenaminothiazol-4-yl)-2-methoxyiminoacetyl chloride.hydrochloride Dimethylformamide (1.6 g, 22 mmol) and 10 ml of tetrahydrofuran were mixed, to which 3.06 g (24 mmol) of oxalyl chloride were added dropwise under ice-cooling. After completion of the dropwise addition, the resulting mixture was stirred for further 10 minutes and was then cooled to −15° C. To the mixture so obtained, were added 2.0 g (10 mmol) of (Z)-2-(2-aminothiazol-4-yl)-2-methoxyiminoacetic acid and 10 ml of tetrahydrofuran, followed by stirring for 80 minutes. The reaction mixture was concentrated under reduced pressure. Slurry was collected by filtration under a nitrogen gas stream and then dried at room temperature, whereby 1.32 g of the title compound were obtained (yield: 43%).

Example 4

Synthesis of (Z)-2-(2-dimethylaminomethyliden aminothiazol-4-yl)-2-methoxyiminoacetyl chloride.hydrochloride Dimethylformamide (0.8 g, 11 mmol) was added to 9 of tetrahydrofuran, followed by ice-cooling. To the resulting mixture, 0.6 ml of trichloromethyl chloroformate was added dropwise under ice-cooling. After stirring the resulting mixture for 30 minutes, the mixture was cooled to −10° C. (Z)-2-(2-Amino-thiazol-4-yl)-2-methoxyiminoacetic acid (840 mg, 4.2 mmol) was added and the mixture so obtained was stirred for 2 hours. The mixture was added with 9 ml of isopropyl acetate, followed by stirring for 30 minutes. A precipitate was collected by filtration under a nitrogen gas stream and then dried at room temperature, whereby 1.23 g of the title compound were obtained (yield: 94%).

Example 5

Synthesis of methyl (Z)-2-(2-dimethylamino methyliden amino thiazol-4-yl)-2-methoxyiminoacetate

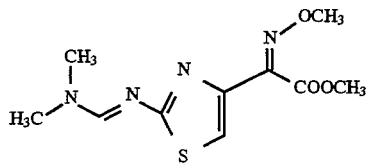

(Z)-2-(2-aminothiazol-4-yl)-2-methoxyiminoacetic acid (0.5 g, 2.5 mmol) was dissolved in 20 ml of tetrahydrofuran. Subsequent to the addition of 0.72 g (9.9 mmol) of dimethylformamide, the resulting solution was cooled to 5° C. The solution was added with 1.52 g (9.9 mmol) of phosphorus oxychloride and the resulting mixture was stirred for 3 hours. Methanol (20 ml) was added to the reaction mixture, followed by stirring for 10 minutes. A 2N aqueous solution of sodium hydroxide was added to the reaction mixture to adjust its pH to 7. The reaction mixture so obtained was extracted three times with 100 ml portions of chloroform. The organic phases were combined and then dried. The solvent was distilled off under reduced pressure. The residue was purified by chromatography on a silica gel column, whereby 0.63 g of the title compound was obtained (yield: 94%).

Syn-isomer $^1$H-NMR (CDCl$_3$, 400 MHz); δ (ppm): 8.30(1H,s), 6.99 (1H,s), 4.00(3H,s), 3.90(3H,s), 3.07(3H,s), 3.03(3H,s). FAB-MS: 271(MH$^+$).

Example 6

Synthesis of methyl (Z)-2-(2-dimethylaminomethylidenaminothiazol-4-yl)-2-methoxyiminoacetate Dimethylaminochloromethyleneammonium chloride (400 mg, 3.1 mmol) was dissolved in 10 ml of tetrahydrofuran, followed by cooling to –3° C. The solution was added with 300 mg (1.5 mmol) of (Z)-2-(2-aminothiazol-4-yl)-2-methoxyiminoacetic acid and the mixture so obtained was stirred for 40 minutes. After the resulting mixture was added with 10 ml of methanol and was then stirred for 10 minutes at room temperature, the mixture was poured into 50 ml of a saturated aqueous solution of sodium hydrogencarbonate. The mixture so obtained was extracted four times with 20 ml portions of chloroform. The extract was dried over anhydrous magnesium sulfate. The dried matter was then concentrated under reduced pressure. The residue was purified by chromatography on a silica gel column, whereby 383 mg of the title compound were obtained (yield: 95%).

Example 7

Synthesis of methyl (Z)-2-(2-dimethylaminomethylidenaminothiazol-4-yl)-2-acetoxyiminoacetate

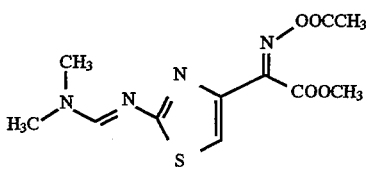

Dimethylaminochloromethyleneammonium chloride (50 mg, 0.39 mmol) was dissolved in 10 ml of tetrahydrofuran. Added to the resulting solution were 99 mg (0.35 mmol) of (Z)-2-(2-aminothiazol-4-yl)-2-acetoxyiminoacetyl.chloride hydrochloride, followed by stirring at room temperature for 40 minutes. Methanol (2 ml) was added thereto. The mixture so obtained was stirred for 10 minutes at room temperature. The mixture was then poured into 50 ml of a saturated aqueous solution of sodium hydrogencarbonate. The mixture so obtained was extracted four times with 20 ml portions of chloroform. The extract was dried over anhydrous magnesium sulfate, and the dried matter was then concentrated under reduced pressure. The residue was purified by chromatography on a silica gel column, whereby 66 mg of the title compound were obtained (yield: 63%).

Syn-isomer $^1$H-NMR (CDCl$_3$, 400 MHz); δ (ppm): 8.33(1H,s), 7.42 (1H,s), 3.98(3H,s), 3.14(3H,s), 3.10(3H,s), 2.21(3H,s).

Example 8

Synthesis of methyl (E)-2-(2-dimethylaminomethylidenaminothiazol-4-yl)-2-methoxyiminoacetate

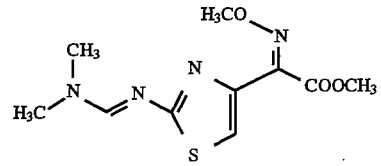

Dimethylaminochloromethyleneammonium chloride (400 mg, 3.1 mmol) was dissolved in 10 ml of tetrahydrofuran. Added to the resulting solution were 300 mg of (Z)-2-(2-aminothiazol-4-yl)-2-methoxyimino-acetic acid, followed by stirring at room temperature for 16 hours. Methanol (10 ml) was added thereto. The mixture so obtained was stirred for 10 minutes at room temperature. The mixture was then poured into 50 ml of a saturated aqueous solution of sodium hydrogencarbonate. The mixture so obtained was extracted four times with 20 ml portions of chloroform. The extract was dried over anhydrous magnesium sulfate. The dried matter was then concentrated under reduced pressure. The residue was purified by chromatography on a silica gelcolumn, whereby 293 mg of the title compound were obtained (yield: 72%).

Anti-isomer $^1$H-NMR (CDCl$_3$ 400 MHz); δ (ppm): 8.15(1H,s), 7.67 (1H,s), 4.07(3H,s), 3.89(3H,s), 3.07(3H,s), 3.06(3H,s).

Example 9

Synthesis of methyl (Z)-2-(2-dimethylaminomethylidenaminothiazol-4-yl) -2-pentenoate

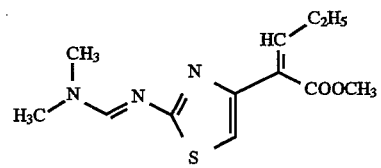

Dimethylaminochloromethyleneammonium chloride (830 mg, 6.5 mmol) was added to 12 ml of tetrahydrofuran, and the resulting mixture was ice-cooled. Added to the mixture were 196 mg (0.99 mmol) of (Z)-2-(2-aminothiazol-4-yl)-2-pentenoic acid, followed by stirring for 1 hour. Methanol (10 ml) was added thereto. The mixture so obtained was stirred for 30 minutes. The mixture was then poured into 60 ml of a saturated aqueous solution of sodium hydrogencarbonate. The mixture so obtained was extracted three times with 40 ml portions of ethyl acetate. The extract was dried over anhydrous magnesium sulfate and was then filtered. The filtrate was concentrated under reduced pressure. The residue was purified by chromatography on a silica gel column, whereby 177 mg of the title compound were obtained (yield: 67%).

$^1$H-NMR (CDCl$_3$, 400 MHz); δ (ppm): 8.22(1H,s), 7.05 (1H,t,J=7.4 Hz), 6.68(1H,s), 3.74(3H,s), 3.09(3H,s), 3.07 (3H,s), 2.31(2H,t-q, J=7.4 Hz), 1.05(3H,t,J=7.4 Hz).

Referential Example 1

Synthesis of p-methoxybenzyl (+)-(6R,7R)-7-[(Z)-2-N,N-dimethylaminomethylidenaminothiazol-4-yl)-2-methoxyiminoacetamido]-3-chloromethyl-8-oxo-5-thia-azabicyclo[4,2,0]oct-2-ene-carboxylate

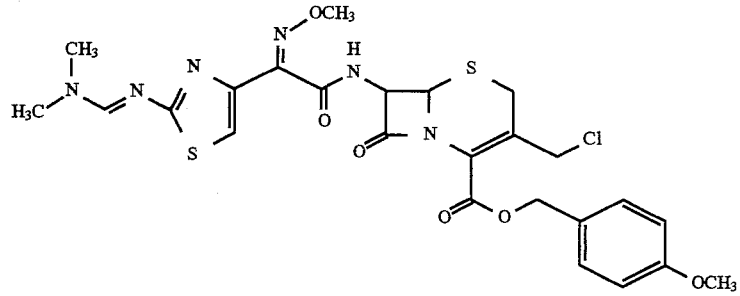

Dimethylaminochloromethyleneammonium chloride (400 mg, 3.1 mmol) was dissolved in 10 ml of tetrahydrofuran, followed by cooling to 3° C. Added to the resulting solution were 300 mg of (Z)-2-(2-aminothiazol-4-yl)-2-methoxyiminoacetic acid and the mixture so obtained was stirred for 2 hours. The resulting solution was added under ice-cooling to a solution of 1.57 g (7.7 mmol) of N,O-bis-trimethylsilylacetamide and 0.56 g (1.4 mmol) of p-methoxybenzyl 7-amino-3-chloromethylcephalosporanoate in tetrahydrofuran, followed by stirring for 6 hours. After 50 ml of water were added, the pH of the resulting mixture was adjusted to 6 with a 2N aqueous solution of sodium hydroxide, followed by extraction with 50 ml of chloroform. The aqueous phase was further extracted twice with 20 ml portions of chloroform. The organic phases were combined and then dried over anhydrous magnesium sulfate. After the dried matter was filtered off, the matter was concentrated under reduced pressure. The residue was dissolved in 50 ml of methanol and the resulting solution was washed three times with 10 ml portions of n-hexane. The methanol phase was concentrated to dryness, whereby 0.97 g of the title compound was obtained (purity: 76.4%).

FAB-MS: 607(MH$^+$). $^1$H-NMR (CDCl$_3$, 400 MHz); δ (ppm): 8.29(1H,s), 7.44(1H,d,J=8 Hz), 7.25(2H,d,J=8 Hz), 7.09(1H,s), 6.81(2H,d,J=8 Hz), 5.88(1H,dd,J=4,8 Hz), 5.13 (2H,s), 4.96(1H,d,J=4 Hz), 4.42(1H, d,J=12 Hz), 4.36(1H, d,J=12 Hz), 3.97(3H,s), 3.72(3H,s), 3.59–3.36(2H,m), 3.00 (3H,s), 2.96(3H,s).

Referential Example 2

Synthesis of 1-(isopropoxycarbonyloxy)ethyl (+)-(6R,7R)-7-[(Z)-2-N,N-dimethylaminomethylidenaminothiazol-4-yl)-2-acetoxyiminoacetamido]-3-N,N-dimethylcarbamoyloxymethyl-8-oxo-5-thiaazabicyclo[4,2,0]oct-2-ene-carboxylate

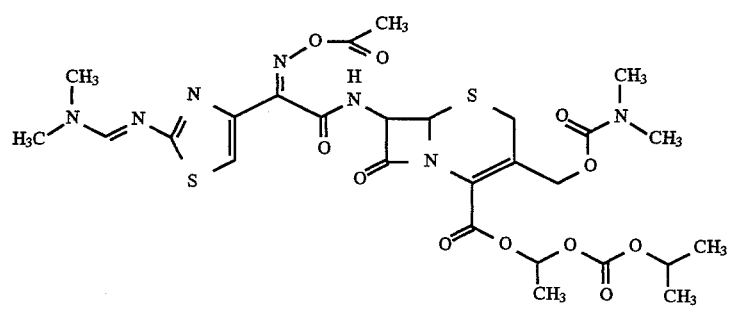

Dimethylaminochloromethyleneammonium chloride (380 mg, 2.97 mmol) was dissolved in 10 ml of tetrahydrofuran, followed by ice-cooling. Added to the resulting solution were 760 mg (2.67 mmol) of (Z)-2-(2-aminothiazol-4-yl)-2-acetoxyiminoacetyl chloride hydrochloride and the mixture so obtained was stirred for 1 hour. The resulting solution was added under ice-cooling to a solution of 2.40 g (11.8 mmol) of N,O-bis-trimethylsilylacetamide and 1.22 g (2.61 mmol) of 1-isopropoxycarbonyloxy 7-amino-3-N,N-dimethylcarbamoyloxymethyl-3-cephem-4-carboxylate hydrochloride in tetrahydrofuran, followed by stirring for 6 hours. After 50 ml of water were added, the pH of the resulting mixture was adjusted to 6 with a saturated aqueous solution of sodium hydrogencarbonate, followed by extraction with 50 ml of ethyl acetate. The aqueous phase was further extracted twice with 50 ml portions of ethyl acetate. The organic phases were combined and then dried over anhydrous magnesium sulfate. After the dried matter was filtered off, the matter was concentrated under reduced pressure. The residue was dissolved in 50 ml of methanol and the resulting solution was washed three times with 10 ml portions of n-hexane. The methanol phase was concentrated to dryness, whereby 0.98 g of the title compound was obtained (purity: 93.3%).

Syn-isomer diastereomer-1

$^1$H-NMR(CDCl$_3$, 400 MHz); δ (ppm): 7.29(1H,d,J=8 Hz), 7.13(1H,s), 6.76(1H,q,J=6 Hz), 5.85(1H,dd,J=4,8 Hz), 4.95–5.06(2H,m), 4.71–4.81(2H,m), 3.47(1H,d,J=20 Hz), 3.38(1H,d,J=20 Hz), 3.00(3H,s), 2.93(3H,s), 2.78(6H,s), 2.10(3H,s), 1.46(3H,d,J=6 Hz), 1.18–1.20(6H,m). FAB-MS; 698 (MH$^+$)

Syn-isomer diastereomer-2

$^1$H-NMR(CDCl$_3$, 400 MHz); δ (ppm): 8.31(1H,d,J=8 Hz), 7.13(1H,s), 6.86(1H,q,J=6 Hz), 5.85(1H,dd,J=4,8 Hz), 4.95–5.06(2H,m), 4.71–4.81(2H,m), 3.47(1H,d,J=20 Hz), 3.38(1H,d,J=20 Hz), 3.00(3H,s), 2.93(3H,s), 2.78(6H,s), 2.10(3H,s), 1.46(3H,d,J=6 Hz), 1.18–1.20(6H,m).

Syn-isomer diastereomer-1

$^1$H-NMR(CDCl$_3$, 400 MHz); δ (ppm): 8.35(1H,s), 7.32 (1H,d,J=12 Hz), 7.14(1H,s), 6.96(1H,q,J=6 Hz), 5.94(1H, dd,J=12,4 Hz), 5.15(1H,d,J=12 Hz), 5.01(1H,d,J=4 Hz), 4.82(1H,d,J=12 Hz), 4.90–4.83(1H,m), 4.02(3H,s), 3.55 (1H,d,J=20 Hz), 3.44(1H,d,J=20 Hz), 3.06(3H,s), 3.01(3H, s), 2.88(3H,s), 2.87(3H,s), 1.54(3H,d,J=6 Hz), 1.28(3H,d, J=6 Hz), 1.26(3H,d,J=6 Hz).

Syn-isomer diastereomer-2

$^1$H-NMR(CDCl$_3$, 400 MHz); δ (ppm): 8.35(1H,s), 7.17 (1H,d,J=8 Hz), 7.14(1H,s), 6.85(1H,q,J=6 Hz), 5.95(1H,dd, J=8,4 Hz), 5.06(1H,d,J=12 Hz), 5.03(1H,d,J=4 Hz), 4.90 (1H,d,J=12 Hz), 4.90–4.83(1H,m), 4.02(3H,s), 3.56(1H,d, J=20 Hz), 3.44(1H,d,J=20 Hz), 3.06(3H,s), 3.01(3H,s), 2.88 (3H,s), 2.87(3H,s), 1.54(3H,d,J=6 Hz), 1.27(3H,d,J=6 Hz), 1.26(3H,d,J=6 Hz).

Referential Example 3

Synthesis of 1-(isopropoxycarbonyloxy)ethyl (+)-(6R,7R)-7-[(Z)-2-dimethylaminomethylidenaminothiazol-4-yl)-2-methoxyiminoacetamido]-3-N,N-dimethylcarbamoyloxymethyl-8-oxo-5-thia-azabicyclo[4,2,0]oct-2-ene-carboxylate

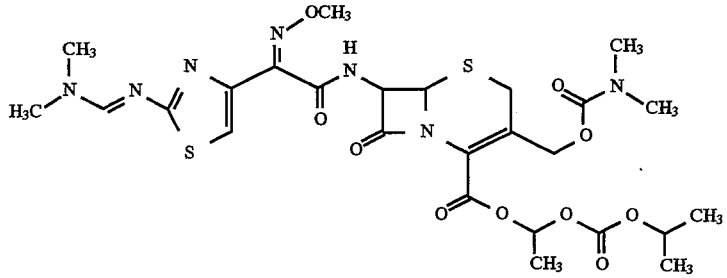

Dimethylaminochloromethyleneammonium chloride (300 mg, 2.3 mmol) was dissolved in 10 ml of tetrahydrofuran, followed by ice-cooling. Added to the resulting solution were 590 mg (2.3 mmol) of (Z)-2-(2-aminothiazol-4-yl)-2-methoxyiminoacetyl chloride hydrochloride and the mixture so obtained was stirred for 1 hour. The resulting solution was added under ice-cooling to a solution of 1.90 g (9.4 mmol) of N,O-bis-trimethylsilylacetamide and 1.0 g (2.1 mmol) of 1-isopropoxycarbonyloxyethyl 7-amino-3-N,N-dimethyl-carbamoyloxymethyl-3-cephem-4-carboxylate monohydrochloride in tetrahydrofuran, followed by stirring: overnight. After 50 ml of water were added, the pH of the resulting mixture was adjusted to 6 with a 2N aqueous solution of sodium hydroxide, followed by extraction three times with 50 ml portions of ethyl acetate. The organic phases combined and then dried over anhydrous magnesium sulfate. After the dried matter was filtered off, the matter was concentrated under reduced pressure. The residue was dissolved in 50 ml of methanol and the resulting solution was washed three times with 10 ml portions of n-hexane. The methanol phase was concentrated to dryness, whereby 1.81 g of the title compound was obtained (purity: 66.8%).

Referential Example 4

Synthesis of 1-(isopropoxycarbonyloxy)ethyl (+)-(6R,7R)-7-[(Z)-2-aminothiazol-4-yl)-2-methoxyiminoacetamido]-3-N,N-dimethylcarbamoyloxymethyl-8-oxo-5-thia-azabicyclo[4,2,0]oct-2-ene-carboxylate

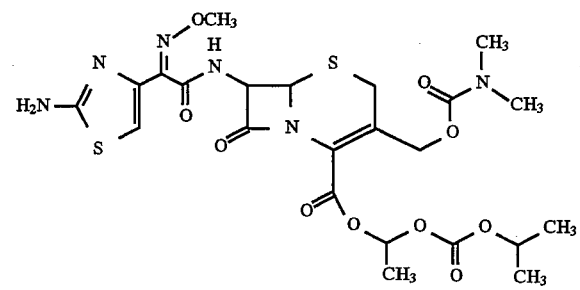

Dissolved in 3 ml of tetrahydrofuran were 40 mg of 1-(isopropoxycarbonyloxy)ethyl (+)-(6R,7R)-7-[(Z)-2- dimethylaminomethylidenaminothiazol-4-yl)-2-methoxyiminoacetamido]-3-N,N-dimethylcarbamoyloxymethyl-8-oxo-5-thia-azabicyclo[4,2,0]oct-2-ene-carboxylate monohydrochloride, followed by the addition of 0.5 ml of 1.8N sulfuric acid. The mixture so obtained was stirred for 3 days at room temperature. The reaction mixture was then added with 50 ml of water and 50 ml of ethyl acetate. The resulting mixture was allowed to separate into an organic phase and an aqueous phase. The aqueous phase was adjusted to pH 7 with a saturated aqueous solution of sodium hydrogencarbonate and then extracted twice with 30 ml portions of ethyl acetate. All the organic phases were combined, dried over anhydrous magnesium sulfate and then concentrated under reduced pressure, whereby the title compound was obtained (purity: 83.3%).

Syn-isomer diastereomer-1

$^1$H-NMR(CDCl$_3$, 400 MHz); δ (ppm): 7.67(1H,d,J=9.0 Hz), 6.92(1H,q,J=5.4 Hz), 6.72(1H,s), 5.96(1H,dd,J=4.9,9.0 Hz), 5.53(2H,br-s), 5.12(1H,d,J=14.0 Hz), 5.00(1H,d,J=4.9 Hz), 5.14–5.00(1H,m), 4.82(1H,d,J=14.0 Hz), 3.98(3H,s), 3.50(1H,d,J=18.8 Hz),3.43(1H,d,J=18.8 Hz), 2.85(6H,s), 1.51(3H,d,J=5.4 Hz), 1.25(3H,d,J=6 Hz), 1.23(3H,d,J=6 Hz).

Syn-isomer diastereomer-2

$^1$H-NMR(CDCl$_3$, 400 MHz); δ (ppm): 7.76(1H,d,J=9.0 Hz), 6.83(1H,q,J=5.4 Hz), 6.72(1H,s), 5.99(1H,dd,J=4.9,9.0 Hz), 5.53(2H,br-s), 5.06(1H,d,J=14.0 Hz), 5.01(1H,d,J=4.9 Hz), 5.14–5.00(1H,m), 4.78(1H,d,J=14.0 Hz), 3.98(3H,s), 3.53(1H,d,J=18.8 Hz),3.43(1H,d,J=18.8 z), 2.85(6H,s), 1.51(3H,d,J=5.4 Hz), 1.25(3H,d,J=6 Hz), 1.24(3H,d,J=6 Hz).

Referential Example 5

Synthesis of (+)-(6R,7R)-7-[(Z)-2-N,N-dimethylaminomethylidenaminothiazol-4-yl)-2-methoxyiminoacetamido]-3-acetoxymethyl-8-oxo-5-thia-azabicyclo[4,2,0]oct-2-ene-carboxylic acid

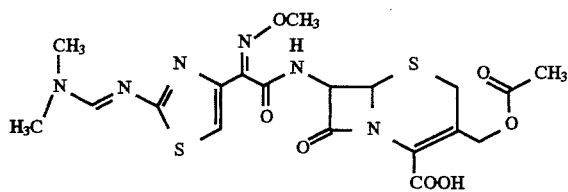

Dimethylaminochloromethyleneammonium chloride (1.14 g, 8.9 mmol) was dissolved in 20 ml of tetrahydrofuran, followed by ice-cooling. Added to the resulting solution were 590 ml (2.3 mmol) of (Z)-2-(2-aminothiazol-4-yl)-2-methoxyiminoacetyl chloride hydrochloride and the mixture so obtained was stirred for 1 hour. To the resulting solution, a solution of 2.45 g (24.3 mmol) of triethylamine and 2.10 g (7.7 mmol) of 7-aminocephalosporanoic acid in tetrahydrofuran was added, followed by stirring for 6 hours under ice-cooling and further for 12 hours at room temperature. Added to the resulting mixture was 1.0 g of triethylamine, and the mixture so obtained was stirred for 3 hours, After 100 ml of a saturated aqueous solution of ammonium chloride were added, the pH of the resulting mixture was adjusted to 6 with acetic acid. The aqueous phase was then washed once with 100 ml of ethyl acetate and further twice with 50 ml portions of ethyl acetate. The aqueous phase was concentrated to about half its volume under reduced pressure. The concentrate was extracted once with 100 ml of methylene chloride and then twice with 50 ml portions of methylene chloride, and further once with 100 ml of ethyl acetate and then twice with 50 ml portions of ethyl acetate. All the organic phases were combined, dried over anhydrous magnesium sulfate and concentrated under reduced pressure, whereby 1.9 g of the title compound was obtained (yield: 48%, purity: 80.2%).

Syn-isomer $^1$H-NMR(CDCl$_3$, 400 MHz); δ (ppm): 8.41(1H,s), 7.21 (1H,s), 7.18(1H,d,J=12 Hz), 5.93(1H,dd,J=12, 4 Hz), 5.10 (1H,d,J=4 Hz), 5.09(1H,d,J=12 Hz), 4.94(1H,d,J=12 Hz), 4.07(3H,s), 3.55(1H,d,J=16 Hz), 3.30(1H,d,J=16 Hz), 3.10 (3H,s), 3.06(3H,s), 2.06(3H,s).

Referential Example 6

Synthesis of N-(2-phenylethyl)-2-(2-dimethylaminomethylidenaminothiazol-4-yl)-2-methoxyiminoacetamide

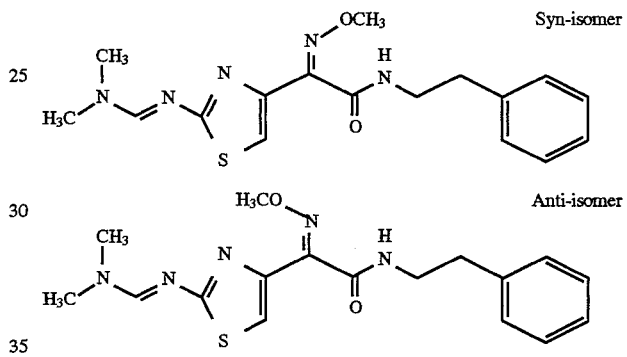

Dimethylaminochloromethyleneammonium chloride (430 mg, 3.36 mmol) was dissolved in 15 ml of tetrahydrofuran. Added to the solution were 860 mg (3.36 mmol) of (Z)-2-(2-aminothiazol-4-yl)-2-methoxyiminoacetyl chloride hydrochloride, followed by stirring at room temperature for 1 hour. To the solution so obtained, a solution of 1.02 g (10.1 mmol) of triethylamine and 0.35 g (2.9 mmol) of β-phenethylamine in 4 ml of tetrahydrofuran was added. The mixture so obtained was stirred for 2 hours under ice-cooling and further for 15 hours at room temperature. The reaction mixture was added with 100 ml of water and then extracted three times with 50 ml portions of chloroform. The organic phases were combined, dried over anhydrous magnesium sulfate and then concentrated under reduced pressure. The residue so obtained was purified by chromatography on a silica gel column, whereby 0.98 g of the title compound was obtained (yield: 95%).

Syn-isomer $^1$H-NMR(CDCl$_3$, 400 MHz); δ (ppm): 8.33(1H,s), 7.31–7.19(5H,m), 6.97(1H,s), 6.19(1H,s), 3.98(3H,s), 3–70 (2H,q,J=8 Hz), 3.07(3H,s), 3.03(3H,s), 2.06(2H,t,J=8 Hz). FAB-MS: 360(MH$^+$)

Anti-isomer $^1$H-NMR(CDCl$_3$, 400 MHz); δ (ppm): 8.07(1H,s), 7.75 (1H,s), 7.64(1H,s), 7.31–7.19(5H,m), 4.05(3H,s), 3.65(2H, q,J=8 Hz), 3.07(3H,s), 3.06(3H,s), 2.91(2H,t,J=8 Hz). FAB-MS: 360(MH$^+$)

Referential Example 7

Synthesis of (Z)-N-(2-phenylethyl)-2-(2-aminothiazol-4-yl)-2-methoxyiminoacetamide

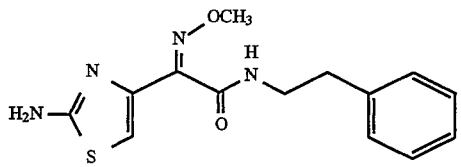

(Z)-N-(2-phenylethyl)-2-(2-dimethylaminomethylidenaminothiazol-4-yl)-2-methoxyiminoacetamide (130 ml, 0.36 mmol) was dissolved in 4 ml of methanol, followed by the addition of 0.5 ml of 1.8N sulfuric acid. The mixture so obtained was stirred for 3 days at room temperature. The reaction mixture was then added with 20 ml of a saturated aqueous solution of sodium hydrogencarbonate and 20 ml of ethyl acetate. The resulting mixture was then allowed to separate into an organic phase and an aqueous phase. The aqueous phase was further extracted twice with 10 ml portions of ethyl acetate. All the organic phases were combined, dried over anhydrous magnesium sulfate and then concentrated under reduced pressure, whereby 105 mg of the title compound were obtained (yield: 95%).
Syn-isomer
$^1$H-NMR(CDCl$_3$, 400 MHz); δ (ppm): 7.35–7.20(5H,m), 6.73(1H,s), 6.11(1H,s), 5.28(2H,br-s), 3.97(3H,s), 3.70(2H, dd,J=8,12 Hz), 2.90(2H,t,J=8 Hz). FAB-MS: 305(MH$^+$)

Referential Example 8

Synthesis of (Z)-N-(2-phenylethyl)-2-(2-aminothiazol-4-yl)-2-methoxyiminoacetamide (Z)-N-(2-Phenylethyl)-2-(2-dimethylaminomethylidenaminothiazol-4-yl)-2-methoxyiminoacetamide (130 mg, 0.36 mmol) was dissolved in 4 ml of methanol, followed by the addition of 1 ml of 2N hydrochloric acid. The mixture so obtained was stirred at 60° C. for 3 hours and 30 minutes. The reaction mixture was then added with 20 ml of a saturated aqueous solution of sodium hydrogencarbonate and 20 ml of ethyl acetate. The resulting mixture was then allowed to separate into an organic phase and an aqueous phase. The aqueous phase was further extracted twice with 10 ml portions of ethyl acetate. All the organic phases were combined, dried over anhydrous magnesium sulfate and then concentrated under reduced pressure, whereby 107 mg of the title compound were obtained (yield: 97.5%).

Referential Example 9

Synthesis of (Z)-N-(2-phenylethyl)-2-(2-aminothiazol-4-yl)-2-methoxyiminoacetamide (Z)-N-(2-Phenylethyl)-2-(2-dimethylaminomethylidenaminothiazol-4-yl)-2-methoxyiminoacetamide (130 mg, 0.36 mmol) was dissolved in 4 ml of methanol, followed by the addition of 0.5 ml of formic acid and 1 ml of water. The mixture so obtained was stirred at 60° C. for 3 hours and 30 minutes. The reaction mixture was then added with 20 ml of a saturated aqueous solution of sodium hydrogencarbonate and 20 ml of ethyl acetate. The resulting mixture was then allowed to separate into an organic phase and an aqueous phase. The aqueous phase was further extracted twice with 10 ml portions of ethyl acetate. All the organic phases were combined, dried over anhydrous magnesium sulfate and then concentrated under reduced pressure, whereby 63 mg of the title compound were obtained (yield: 57.9%).

Referential Example 10

Synthesis of (Z)-N-(2-phenylethyl)-2-(2-aminothiazol-4-yl)-2-methoxyiminoacetamide (Z)-N-(2-Phenylethyl)-2-(2-dimethylaminomethylidenaminothiazol-4-yl)-2-methoxyiminoacetamide (130 mg, 0.36 mmol) was dissolved in 4 ml of methanol, followed by the addition of 1 ml of a 1N aqueous solution of sodium hydroxide. The mixture so obtained was stirred at room temperature for 2 days. The reaction mixture was then added with 20 ml of a saturated aqueous solution of ammonium chloride and 20 ml of methylene chloride. The resulting mixture was then allowed to separate into an organic phase and an aqueous phase. The aqueous phase was further extracted twice with 10 ml portions of methylene chloride. All the organic phases were combined, dried over anhydrous magnesium sulfate and then concentrated under reduced pressure, whereby 90 mg of the title compound were obtained (yield: 81.8%).

What is claimed is:

1. A protected aminothiazolylacetic acid derivative represented by the following formula (I):

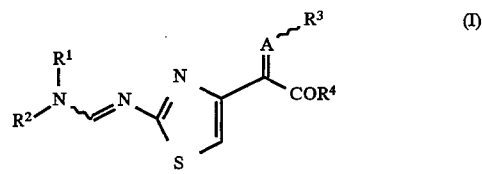

wherein A represents a nitrogen atom $R^1$ and $R^2$ may be the same or different and individually represent a hydrogen atom, a lower alkyl group or a substituted or unsubstituted aryl group, $R^3$ represents a lower alkoxy group, a halogenated lower alkoxy group, a triphenylmethoxy group, or an acyloxy group, and $R^4$ represents a halogen atom, a hydroxy group, or a substituted or unsubstituted amino group; or a salt thereof.

* * * * *